US008611619B2

(12) United States Patent
Ljung

(10) Patent No.: US 8,611,619 B2
(45) Date of Patent: Dec. 17, 2013

(54) READ-OUT METHOD AND APPARATUS

(75) Inventor: Arne Ljung, Uppsala (SE)

(73) Assignee: Phadia AB, Uppsala (SE)

( * ) Notice: Subject to any disclaimer, the term of this patent is extended or adjusted under 35 U.S.C. 154(b) by 830 days.

(21) Appl. No.: 12/674,031

(22) PCT Filed: Aug. 21, 2008

(86) PCT No.: PCT/SE2008/050944
§ 371 (c)(1),
(2), (4) Date: Feb. 18, 2010

(87) PCT Pub. No.: WO2009/025616
PCT Pub. Date: Feb. 26, 2009

(65) Prior Publication Data
US 2010/0284583 A1    Nov. 11, 2010

(30) Foreign Application Priority Data

Aug. 22, 2007  (SE) ...................... 0701899

(51) Int. Cl.
*G06K 9/00*   (2006.01)
(52) U.S. Cl.
USPC ......................................... 382/128
(58) Field of Classification Search
None
See application file for complete search history.

(56) References Cited

U.S. PATENT DOCUMENTS 4,800,279 A * 1/1989 Hieftje et al. ............. 250/339.09
5,304,468 A * 4/1994 Phillips et al. ................. 435/14
5,408,535 A * 4/1995 Howard et al. ............... 382/128
5,717,778 A * 2/1998 Chu et al. ..................... 382/133
5,917,541 A * 6/1999 Nakagome et al. ............. 348/93
6,249,593 B1 * 6/2001 Chu et al. ..................... 382/128
6,850,633 B2 * 2/2005 Schrier et al. ................. 382/128

(Continued)

FOREIGN PATENT DOCUMENTS

JP       2000266752 A     9/2000
JP       2003506715 A     2/2003

(Continued)

OTHER PUBLICATIONS

X. Zhao et al., "A 0.18um CMOS on-chip skin detection scheme based on NPNP-triple-junction structure", the International Symposium on Integrated Circuits (ISIC 2007), Singapore, Sep. 2007, pp. 333-336.

(Continued)

*Primary Examiner* — Robert Morgan
*Assistant Examiner* — Michael Tomaszewski
(74) *Attorney, Agent, or Firm* — Young & Thompson

(57) ABSTRACT

A read-out method for a diagnostic point-of-care assay device, the device including a read-out substrate having at least one response area capable of producing a colored indication of a response, the response area including a marker at least one marker whose color changes in response to binding of an analyte thereto and which is used for indication of response. The method includes registering an image of the response area; calculating a color saturation value S for the image using at least two distinct wavelengths; using the S-value for determining a result of the assay. A read-out system (10) for an allergy point-of-care assay device is described. The system includes an illumination device (12; 21, 22) capable of delivering at least two different wavelengths of light; a color image capturing device (14); a control unit (19) for calculating a color saturation value on images recorded by the color image capturing device.

10 Claims, 4 Drawing Sheets

(56) References Cited

U.S. PATENT DOCUMENTS

| | | | |
|---|---|---|---|
| 6,861,264 B2* | 3/2005 | Mabile et al. | 436/172 |
| 7,613,335 B2* | 11/2009 | McLennan et al. | 382/128 |
| 7,803,633 B2* | 9/2010 | Spivey et al. | 436/164 |
| 2001/0002315 A1* | 5/2001 | Schultz et al. | 436/172 |
| 2001/0034068 A1* | 10/2001 | Spivey et al. | 436/518 |
| 2002/0031783 A1* | 3/2002 | Empedocles et al. | 435/7.1 |
| 2002/0168784 A1* | 11/2002 | Sundrehagen et al. | 436/536 |
| 2003/0165263 A1* | 9/2003 | Hamer et al. | 382/133 |
| 2004/0038241 A1* | 2/2004 | Glennsbjerg | 435/6 |
| 2010/0045789 A1* | 2/2010 | Fleming et al. | 348/79 |

FOREIGN PATENT DOCUMENTS

| | | | | |
|---|---|---|---|---|
| JP | 2006250765 A | 9/2006 | | |
| WO | 0111359 A2 | 2/2001 | | |
| WO | WO 2009025616 A1 * | 2/2009 | | G01N 33/543 |

OTHER PUBLICATIONS

Translation of Japanese Office Action, dated May 14, 2013, from corresponding JP application.

* cited by examiner

READ-OUT METHOD AND APPARATUS

FIELD OF THE INVENTION

The present invention relates to a method of obtaining a reliable read-out from a composite signal represented by a coloured area on a test member, the colour being obtained as a response to an analyte.

BACKGROUND OF THE INVENTION

For many diagnostic applications colour or colour change is used as an indication of presence or absence of an analyte in a biologic test sample, such as blood (serum, plasma, whole blood), saliva, tear fluid, urine, cerebrospinal fluid, sweat, etc.

For point-of-care applications where it is desirable to obtain a quick read-out of a test, it is essential that the read-out is clear and unambiguous. There are many applications commercially available which are based on simple test strips onto which a sample is applied, whereupon migration of the sample in the strip brings analytes in contact with a reagent, the response being a colour in case of a positive reaction, i.e. presence of the analyte in question.

It goes without saying that the more reliable, i.e. clear and unambiguous the response is the better it is. Sometimes a test is of a binary nature, such as for pregnancy tests, where there can be only a positive or a negative result. On the other hand, for tests such as allergy tests, there can be a range of levels of the response in dependence on how high the concentration of antibodies in the patient's serum is.

A common marker for use in e.g. allergy or autoimmune tests is a so called gold conjugate, comprising a colloidal gold particle in the nanometer size range, to which a protein (antibody or antigen) has been coupled ("conjugated"). The conjugate gives rise to some detectable signal when the desired analyte is coupled thereto in the assay.

For certain samples where a clear colour indication normally is obtained if there is a positive response, it can sometimes happen that there are other species (frequently the allergens themselves) present that will give rise to gray lines which can be difficult to distinguish from pink lines. This "blurs" the true signal. Thus, one can obtain false positive or false negative results, which of course can be of consequences if the test is to form the basis for a treatment regimen.

SUMMARY OF THE INVENTION

The object of the present invention is to provide a method and a device for providing reliable read-out from test systems of the kind discussed in the preamble, i.e. that will eliminate the problem of erroneous read-outs.

This object is achieved in a first aspect, namely a read-out method for a diagnostic point-of-care assay device, the device comprising a read-out substrate having at least one response area capable of producing a coloured indication of a response, the response area comprising a marker at least one marker the colour of which changes in response to binding of an analyte thereto and which is used for indication of response, the method comprising the steps of registering an image of said response area; calculating a colour saturation value S for said image using at least two wave length ranges (colours); using the S-value for determining a result of the assay. Suitably the S-values are compared with a selected threshold value G. Furthermore, the S-value(s) is/are suitably correlated to a physical quantity to obtain a value for said physical quantity. The wavelengths are in preferred embodiments selected such that one wavelength has an absorption maximum for the marker used in the assay, and the other wavelengths have a significantly lower absorption for the marker. Most preferably two wavelengths are used. The marker is preferably a gold conjugate.

In a second aspect the invention provides a read-out system, comprising an illumination device capable of delivering at least two different wavelengths of light, a colour image capturing device, and a control unit for calculating a colour saturation value (S) on images recorded by the colour image capturing device.

BRIEF DESCRIPTION OF THE DRAWING FIGURES

The major advantage with the present invention is that there is no need for skilled or trained staff to perform readings of the assay.

Further scope of applicability of the present invention will become apparent from the detailed description given hereinafter and the accompanying drawings which are given by way of illustration only, and thus not to be considered limiting on the present invention, and wherein FIG. 1 illustrates schematically a first embodiment of a read-out set-up according to the invention;

DETAILED DESCRIPTION OF PREFERRED EMBODIMENTS

Figure 1:
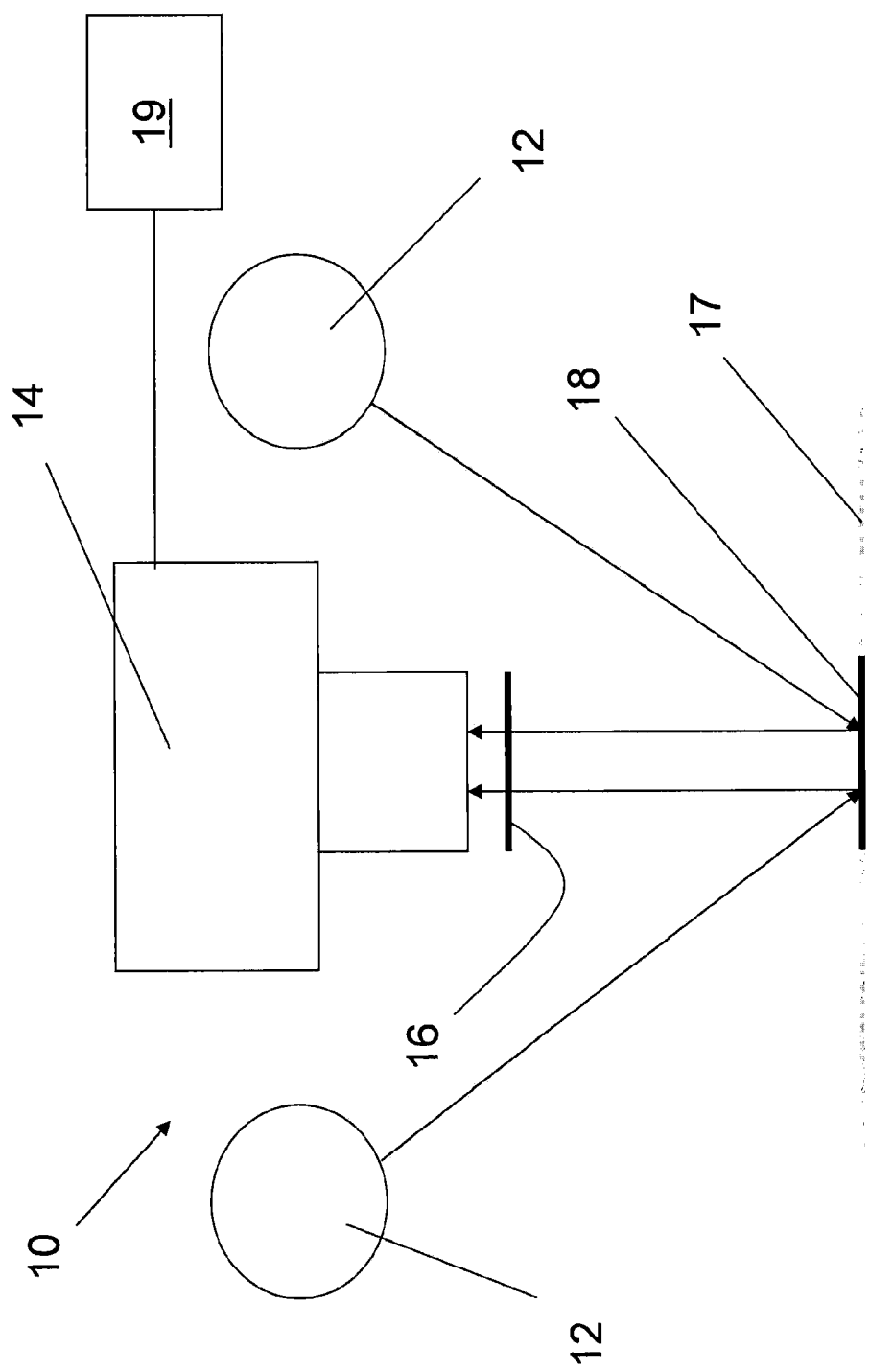

First a brief review of different colour systems (colour spaces) will be given.

The RGB colour model is an additive model in which red, green, and blue (often used in additive light models) are combined in various ways to reproduce other colours. The name of the model and the abbreviation 'RGB' come from the three primary colours, red, green, and blue. These three colours should not be confused with the primary pigments of red, blue, and yellow, known in the art world as 'primary colours'.

The RGB colour model itself does not define what is meant by 'red', 'green' and 'blue', and the results of mixing them are not exact unless the exact spectral make-up of the red, green and blue primaries are defined.

The HSV (Hue, Saturation, Value) model, also known as HSB (Hue, Saturation, Brightness), defines a colour space in terms of three constituent components:

Hue, the colour type (such as red, blue, or yellow):
Ranges from 0-360° (but normalized to 0-100% in some applications)

Saturation, the "vibrancy" of the colour: Ranges from 0-100%. Also sometimes called the "purity" by analogy to the colourimetric quantities excitation purity and colourimetric purity. The lower the saturation of a colour, the more "grayness" is present and the more faded the colour will appear, thus useful to define desaturation as the qualitative inverse of saturation.

Value, the brightness of the colour. Ranges from 0-100%.

The HSV model is a nonlinear transformation of the RGB colour space, and may be used in colour progressions. Note that HSV and HSB are the same, but HSL is different.

The HSL colour space, also called HLS or HSI, stands for Hue, Saturation, Lightness (also Luminance or Luminosity)/

Intensity. While HSV (Hue, Saturation, Value) can be viewed graphically as a colour cone or hexcone, HSL can be drawn as a double cone or double hexcone as well as a sphere. Both systems are non-linear deformations of the RGB colour cube.

The definition of the HSV colour model is not device independent. HSV is only defined relative to RGB intensities—without physical definitions of their chromaticities and white point. For accurate and device independent representation, use CIE L*a*b or another CIE-based colour model.

In software, a hue-based colour model (HSV or HSL) is usually presented to the user in the form of a linear or circular hue chooser and a two-dimensional area (usually a square or a triangle) where you can choose saturation and value/lightness for the selected hue. With this representation, the difference between HSV or HSL is irrelevant. However, many programs also let you select a colour via linear sliders or numeric entry fields, and for those controls, usually either HSL or HSV (not both) are used. HSV is traditionally more common.

The present invention is makes use of the notion of colour saturation, and the HSV model is used for analysing an image. The invention is generally applicable to the analysis of coloured "spots" on e.g. assay strips, and will now be described below exemplified by two embodiments.

The present invention has particular utility for so called Point of Care (PoC) assay devices for detecting allergy. Such assay devices typically consists of a plastic casing having a bibulous (porous) strip provided therein, which is exposed through a window in the casing. A liquid sample (e.g. blood, plasma, or any other suitable liquid) is placed in a sample well, and is caused to migrate by capillary forces along the strip, where it encounters and reacts with allergens at predefined locations, commonly narrow transverse lines across the strip. A reagent causing a colour change is also provided such that the reaction becomes visible.

For determining the position of the window one could use fixed coordinates for the window. However, this places very high requirements on the mechanical precision on the read-out device and on the assay device.

Alternatively, and preferably, image processing methods can be used to locate the position of the window In the Figures elements that are common to both embodiments have been given the same reference numeral.

Figure 2:
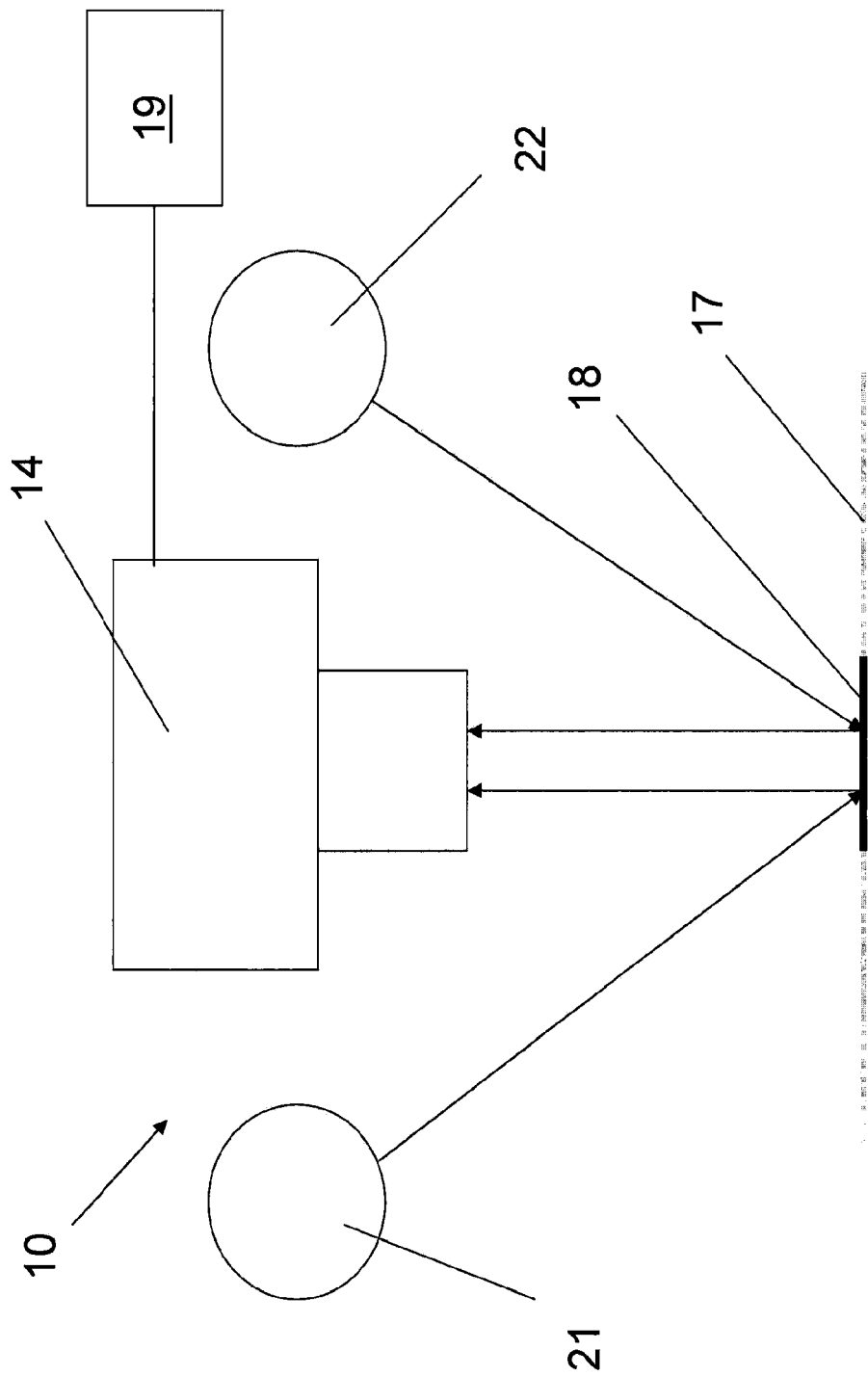
FIG. 2 illustrates schematically a second embodiment of a read-out set-up according to the invention.

A detection set-up or apparatus for obtaining a read-out from an assay device according to the invention is disclosed in FIGS. 1 and 2, each showing a respective embodiment thereof.

The read-out system, generally designated 10, according to the first embodiment of the invention shown in FIG. 1 comprises one or more (two shown) sources 12 of white light, an image sensor 14, suitably a digital camera (although of course other kinds of image sensor are possible too), a filter unit 16 comprising at least two selectable filters for different wavelengths. The filter unit can be integrated in the image sensor (camera) or provided separately. Also shown in FIG. 1 is the assay strip 17 with its detection area 18.

In this first embodiment the detection area 18 of the assay strip is illuminated, as indicated by arrows, and the light reflected from the detection area, also shown by arrows, is passed through a filter, and the resulting image is recorded. One image is recorded for each filter used so as to obtain two images with different colour saturation.

In the second embodiment of the read-out system 10 according to the invention shown in FIG. 2, there is no filter unit. Instead two light sources 21, 22 of different wavelengths are used, and one image is recorded for each wavelength.

The choice of wavelengths is dependent on the marker used, and should be selected such that one wave-length $\lambda_1$ is one that has a maximum absorption for the used marker. The other wavelength $\lambda_2$ (in case of two markers) should have a low absorption for the marker, but be relatively close to the first wavelength, suitably not more than 300 nm from the first wave length, i.e. $\lambda_2$ is within $\lambda_1 \pm 300$ nm, preferably not more than 100 nm from the first wavelength, i.e. $\lambda_2$ is within $\lambda_1 \pm 100$ nm.

For the processing and evaluation of the recorded image there is provided a control unit, e.g. a personal computer or dedicated control unit in the form of a micro processor 19. The control unit is programmed to perform a calculation of a saturation (S) value for the recorded image.

Generally, the method according to the invention comprises registering one or more images of the response area 18 on the assay device 17. Then, a colour saturation value S for said images is calculated, using at least two distinct colours (wavelengths). Finally, the S-value is used for determining a result of the assay.

For the evaluation of the recorded images a method can be used, based on the HSV colour system, discussed above.

In particular the S-value is given by $$S = \frac{\text{MAX} - \text{MIN}}{\text{MAX}} = 1 - \frac{\text{MIN}}{\text{MAX}}$$

using the HSV system; wherein MAX is the largest value for the intensity of the two registered wavelengths, and MIN is the smallest.

In a specific embodiment of the read-out system, the formula for calculating S can be simplified to $S = 1 - \text{Green}/\text{Red}$ This is possible in the case where it is known which hue-range the response lines comprising gold conjugate will be in, and also it is known in which hue and saturation range the background colour will be in.

In this formula "Green" is the value of the green channel in one RGB colour system and Red is the value of the red channel in that RGB colour system.

In particular for this simplification to hold, the Hue should meet the requirement $300° < \text{Hue} < 60°$.

For an assay of the type with which the present invention is concerned there can be several causes of errors. There are three major causes of errors, namely, 1) insufficient flow of plasma over the strip—lower peak values
2) insufficient flow of conjugate—lower peak values
3) unsatisfactory wash—higher background In particular these phenomena may be of different magnitude across the strip, i.e. they will cause varying degree of reaction in the allergen zones, thus causing a varying colour intensity across the strip.

Stripes of interfering colours can also occur along the flow on the strip, which will cause the background to be too high. The origin of such stripes can be conjugate that remains in the matrix due to insufficient wash.

However, all these possible errors will cause a decrease in the colour values of the actual assay lines, which can be used to advantage.

Namely, in order to handle the above possible errors, when the exact position of the strip window has been determined and the image has been converted into a colour saturation image, the image of the strip in the response area is subdivided in a number of sub-strips. The number of sub-strips can vary from a few and up to say 20 or 30. Suitably the number of strips is 5-25, more preferably 8-20, most preferred 10-15. In a practical embodiment 13 strips have been used.

For each sub-strip peak values are determined for all allergen lines on the assay together with background values. The difference between peak and background is calculated for each line and strip. All sub-strips are compared and the highest value for a respective line, is selected as a "true" value for that line.

The invention is applicable to any type of assay device that provides a visible (coloured) response. Preferably the assay device comprises a test strip on which a sample can migrate from a point of application of the sample through a reaction zone and to a detection zone in which the coloured response is visible as a spot or a band. Other kinds of assay are possible so long as they result in a coloured entity that can be recorded as an image, or the colour saturation of which can be measured.

In particular it can be used for assessing presence or absence of an analyte in a biologic test sample, such as blood (serum, plasma, whole blood), saliva, tear fluid, urine, cerebrospinal fluid, sweat, etc.

The invention is, of course, also applicable to other types of samples, such as fermentation solutions, reaction mixtures, etc. Especially, however, the sample is an undiluted serum or whole blood sample.

The marker that is used in the assay could in principle be any kind of marker that delivers a colour response. Preferably the marker is a gold conjugate. The marker is immobilized in a detection zone on a test strip and when an analyte migrates along the strip and contacts the marker a colour change is brought about.

EXAMPLES

In the Examples below a set-up consisting of a Canon EOS 350D camera as the image sensor. Illumination was provided by a Luxeon Star LXHL-LW3C LED-lamp giving a white light. Two filters were used, one operating at 530 nm and the other at 610 nm (The green and red filters at the Canon 350D image sensor). The test device was an allergy POC assay (ImmunoCAP Rapid Wheeze/Rhinitis Child).

Example 1

A plurality of samples from different patients suspected of having birch pollen allergy was placed on POC assay strips, and visible read-outs were generated.

A panel of test persons (A, B, C, D) were given the read-outs for visual evaluation, the results are given in Table 1 below.

The same assay strips was analysed with a set-up according to the invention, and the result was an unambiguous reading. The result is given in Table as comparison to the visual assessments.

Example 2

Figure 3:
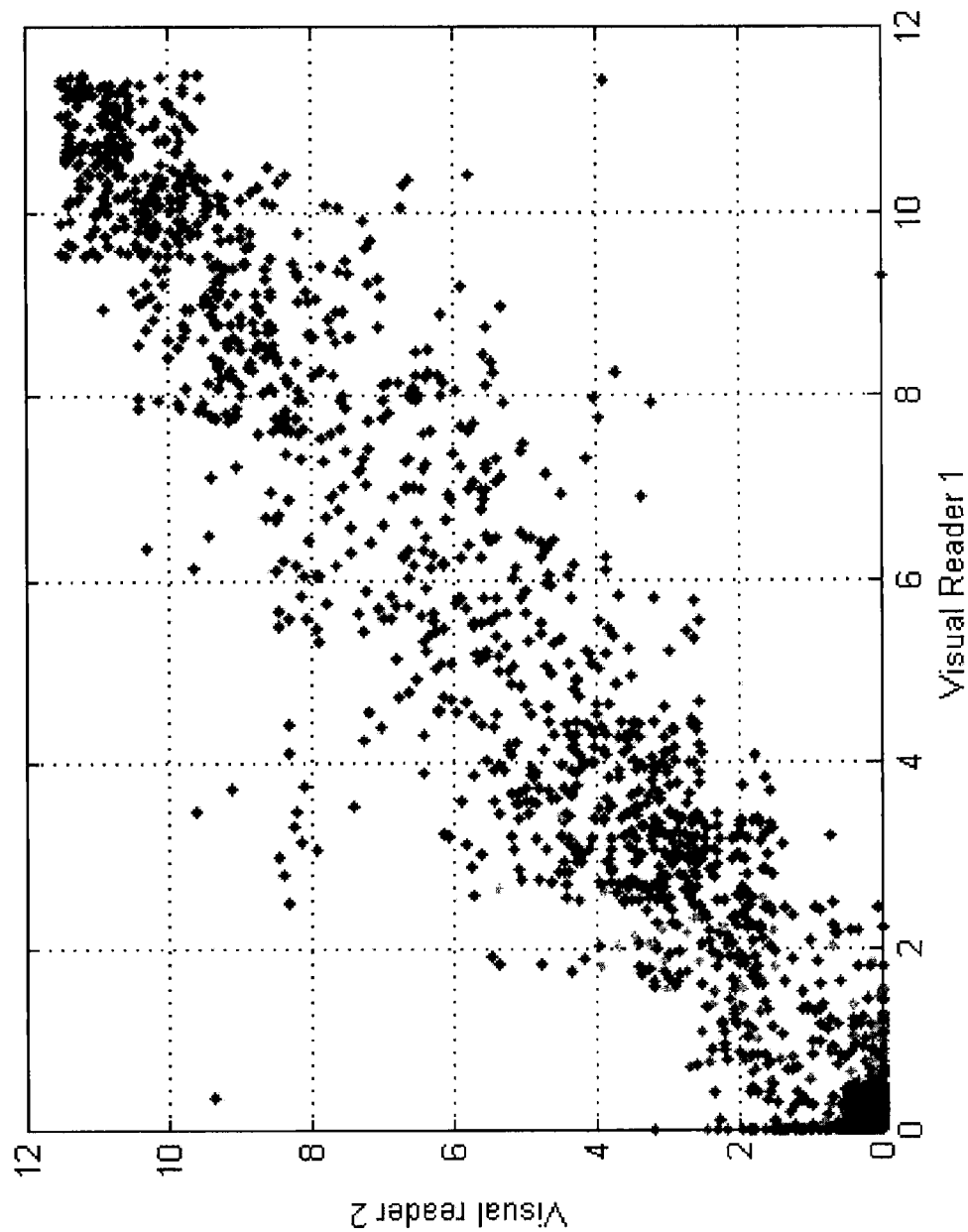
FIG. 3 is a plot of a comparison between two experienced "visual readers"

FIG. 3 is a graph showing a comparison between two experienced "visual readers", assessing the same test devices, where the readings are made on a scale of 0-12, and each device having 12 spots. The reading of Visual Reader 1 is plotted against the reading of the same test device by Visual reader 2. To present the visual (integer) values, noise has been added to spread out the values to show the density of reading in different areas of the diagram. This figure clearly illustrates the degree of uncertainty in visual readings, and shows the need of ways and means to obtain more consistent readings in order to avoid misinterpretations.

Example 3

Figure 4:
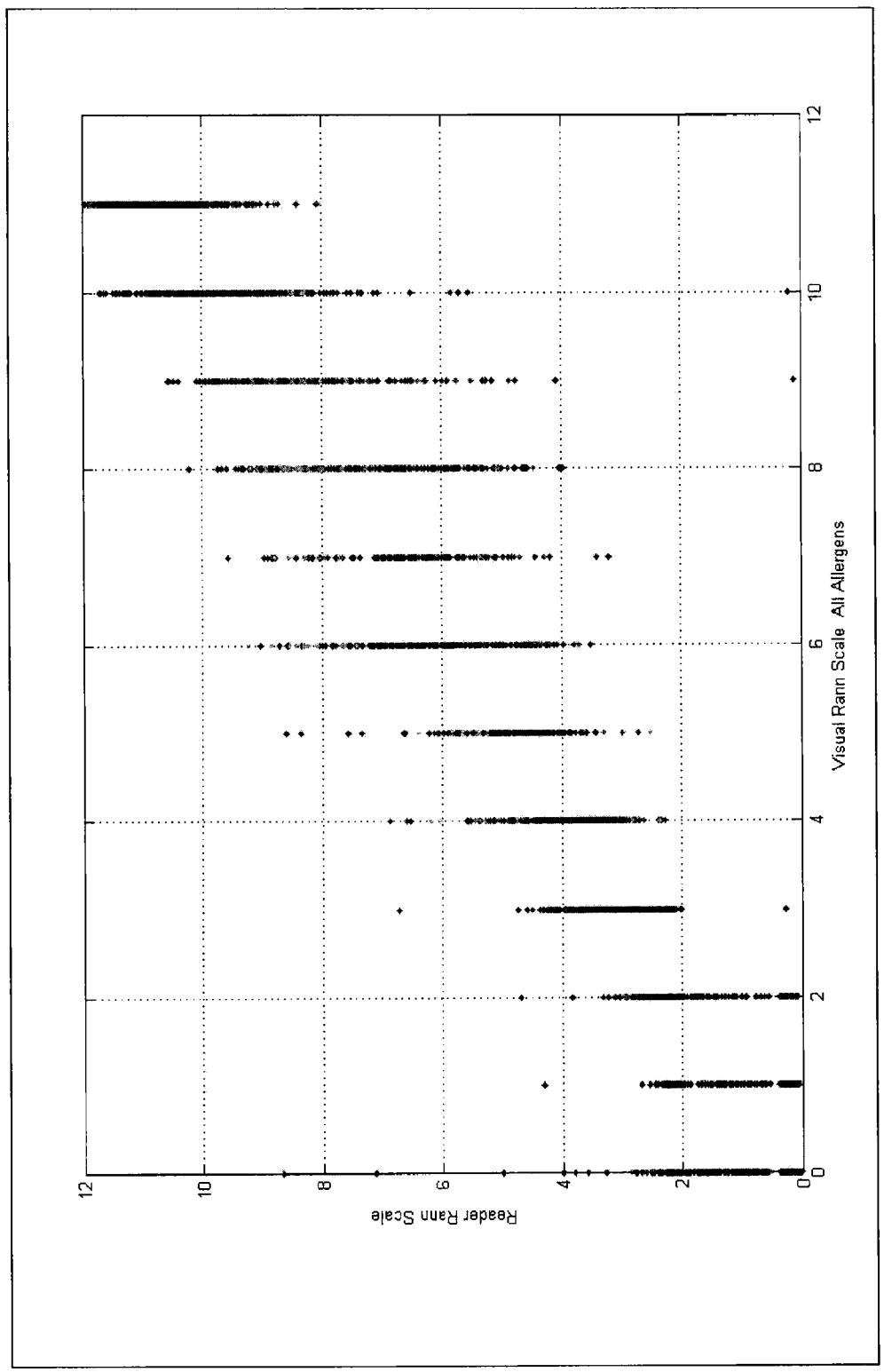
FIG. 4 is a plot of visual reader vs automated reader according to the invention.

FIG. 4 is a graph showing readings by the device according to the invention plotted against readings made by an experienced visual reader.

The Table below shows averages of about 1000 readings (from FIG. 3) for a visual reader and an automated reader according to the invention. The table shows the mean value from the automated reader (AR) according to the invention for each of the visual readings (VR) of integer values 0 to 11.

| VR | 0 | 1 | 2 | 3 | 4 | 5 | 6 | 7 | 8 | 9 | 10 | 11 |
|---|---|---|---|---|---|---|---|---|---|---|---|---|
| AR | 0.22 | 0.93 | 2.08 | 2.95 | 3.94 | 4.79 | 5.81 | 6.44 | 7.42 | 8.43 | 9.56 | 10.98 |

This illustrates that the method and device according to the invention is comparable with experienced visual readers.

The invention claimed is:

1. A method for detecting the presence and/or amount of an analyte in a sample by obtaining a reliable read-out from a composite signal represented by a coloured area on a test member, the colour being obtained as a response to the analyte, the method comprising:
   providing as said test member a read-out substrate in the form of a bibulous strip having at least one response area and at least one marker on said response area, the marker causing a colour change when the analyte in the sample undergoes a reaction;
   applying a liquid sample, blood, plasma, or any other suitable liquid containing an analyte, on said strip, whereby said sample is caused to migrate by capillary forces along the strip, and undergoes a reaction at predefined locations on said strip;
   illuminating the assay strip;
   recording an image of said strip;
   calculating a colour saturation value S for said image using said at least two wavelength ranges; the S-value being calculated as $$S = \frac{MAX - MIN}{MAX} = 1 - \frac{MIN}{MAX}$$

using the "Hue, Saturation, Value" (HSV) system; wherein MAX is the largest value for the intensity of the at least two registered wavelengths, and MIN is the smallest; and
   using the S-value for determining a result of the assay by comparing the S-values with a selected threshold value G, and correlating the S-value to a physical quantity.

2. The method as claimed in claim 1, wherein the wavelengths are selected such that one wavelength has an absorption maximum for the marker used in the assay, and the other wavelengths have a significantly lower absorption for the marker.

3. The method as claimed in claim 1, wherein two wavelengths are used.

4. The method as claimed in claim 1, wherein the marker is a gold conjugate.

5. The method as claimed in claim 1, wherein the image of the response area is subdivided in a number of sub-strips.

6. The method as claimed in claim 5, wherein the number of sub-strips is between 5 and 30.

7. The method as claimed in claim 1, wherein peak values are determined for each sub-strip and for all allergen lines together with background values, the difference between peak and background is calculated for each line and strip, and all sub-strips are compared and the highest value for a respective line, is selected as a "true" value for that line.

8. A read-out system (10) for an allergy point-of-care assay device (17, 18), using colour change on a test member as an indication of presence or absence of an analyte, the system comprising:
   an illumination device (12; 21, 22) capable of delivering at least two different wavelengths of light;
   a colour image capturing device (14); and
   a control unit (19) for calculating a colour saturation value (S) on images recorded by the colour image capturing device, the control unit being adapted to calculate the S-value as $$S = \frac{MAX - MIN}{MAX} = 1 - \frac{MIN}{MAX}$$

using the "Hue, Saturation, Value" HSV system; wherein MAX is the largest value for the intensity of the at least two different wavelengths, and MIN is the smallest, and
   using the S-value for determining a result of the assay by comparing the S-values with a selected threshold value G, and correlating the S-value to a physical quantity.

9. The read-out system as claimed in claim 8, wherein the illumination device comprises at least two light sources (21, 22) delivering light of different wave-lengths.

10. The read-out system as defined in claim 8, wherein the illumination device comprises a source of white light and at least two filters for filtering out selected wavelengths from an image.

* * * * *